United States Patent [19]

Ketharanathan

[11] Patent Number: 4,681,588
[45] Date of Patent: Jul. 21, 1987

[54] BIOMATERIAL

[76] Inventor: Vettivetpillai Ketharanathan, 35 Degraves Street, Parkville, Victoria, Australia

[21] Appl. No.: 760,745
[22] PCT Filed: Oct. 17, 1984
[86] PCT No.: PCT/AU84/00206
§ 371 Date: Jun. 17, 1985
§ 102(e) Date: Jun. 17, 1985
[87] PCT Pub. No.: WO85/01651
PCT Pub. Date: Apr. 25, 1985

[30] Foreign Application Priority Data

Oct. 20, 1983 [AU] Australia ............................ PG1955

[51] Int. Cl.$^4$ .......................... A61F 2/02; A61F 2/06; A61B 19/00; A61L 17/00
[52] U.S. Cl. ........................................ 623/11; 623/1; 623/66; 128/1 R; 8/94.11
[58] Field of Search .............. 424/95; 8/94.11; 623/1, 623/2, 11, 15, 66; 128/334 R, 1 R

[56] References Cited

U.S. PATENT DOCUMENTS

| | | | |
|---|---|---|---|
| 3,093,439 | 6/1963 | Bothwell | 8/94.11 |
| 3,974,526 | 8/1976 | Dardik et al. | 3/1.4 |
| 3,988,782 | 11/1976 | Dardik et al. | 3/1 |
| 4,120,649 | 10/1978 | Schechter | 623/2 X |
| 4,275,469 | 6/1981 | Gabbay | 623/2 |
| 4,466,139 | 8/1984 | Ketharanathan | 3/1.4 |
| 4,477,930 | 10/1984 | Totten et al. | 623/2 |

FOREIGN PATENT DOCUMENTS

| | | |
|---|---|---|
| 0052288 | 5/1982 | European Pat. Off. . |
| WO82/00091 | 1/1982 | PCT Int'l Appl. . |
| 2063675 | 6/1981 | United Kingdom . |

OTHER PUBLICATIONS

Stedman's Medical Dictionary, 24th ed., 1982, Williams & Wilkins Co. Baltimore, p. 1053.

Primary Examiner—Richard J. Apley
Assistant Examiner—Alan W. Cannon
Attorney, Agent, or Firm—Nixon & Vanderhye

[57] ABSTRACT

Material for use in a biological environment is produced by subjecting a sheet of parietal pleura to glutaraldehyde tanning. The pleura is stretched and cleansed of excessive tissue to result in a membrane of substantially uniform thickness prior to tanning.

The material produced by the invention may be used as a surgical graft material, in which case the visceral surface of the pleura may provide a blood contacting surface. The material may also be used as a surgical dressing.

The pleura may be obtained from various animal species but will commonly be bovine pleura.

12 Claims, 10 Drawing Figures

BIOMATERIAL

TECHNICAL FIELD

This invention provides a novel kind of material for use in a biological environment. More particularly this material may be used in treatments of the human body for example as a surgical dressing or for the repair of herniae, heart valves, holes in the heart or other defects. In some cases the material produced in accordance with the present invention may be used for dialysis and other filtering procedures.

DISCLOSURE OF INVENTION

The material of the present invention comprises a sheet of an animal parietal pleura which has been subjected to glutaraldehyde tanning. The invention also extends to the use of such material as a surgical graft or as a dressing applied to a living human patient.

The invention also provides a method of producing a biocompatible material comprising subjecting a sheet of animal parietal pleura to glutaraldehyde tanning.

The material may be subjected to irradiation before or after the glutaraldehyde tanning treatment. It may for example be subjected to 0.2 to 5.0 megarads of irradiation.

To be of maximum value, a biomaterial should be:

| | |
|---|---|
| 1. | Shelf storable. |
| 2. | Available in a wide range of sizes and shapes. |
| 3. | Sterile. |
| 4. | Non-antigenic. |
| 5. | Available in biodegradable or non-biodegradable form as the situation demands. |
| 6. | Able to support epithelial or endothelial growth as the situation demands. |

By treating parietal pleura in accordance with the present invention it is possible to produce biomaterial meeting the above requirements.

Pleura is a thin membranous lining of the thoracic cavity and lungs. The pleura covering the thoracic cavity is termed parietal pleura and that covering the lungs is termed visceral. The invention makes use of the parietal pleura which consists of loose connective tissue covered with a single layer of mesothelial cells. The other components that are found in the connective tissue are macrophages, blood vessels, lymphatics, nerve fibres and fat cells.

In some circumstances human pleura may be available but more generally parietal pleura will be obtained from freshly slaughtered carcasses of animals such as cattle, sheep and pigs. In this way it has been possible to obtain sheets of pleura that measure as much as 60 cm × 60 cm square. For special uses pleura can also be obtained from foetal calves.

BRIEF DESCRIPTION OF DRAWINGS

In the following detailed description of examples of clinical use of material prepared in accordance with the invention, reference will be made to the accompanying illustrations in which.

BEST MODES OF CARRYING OUT THE INVENTION

Figure 1:
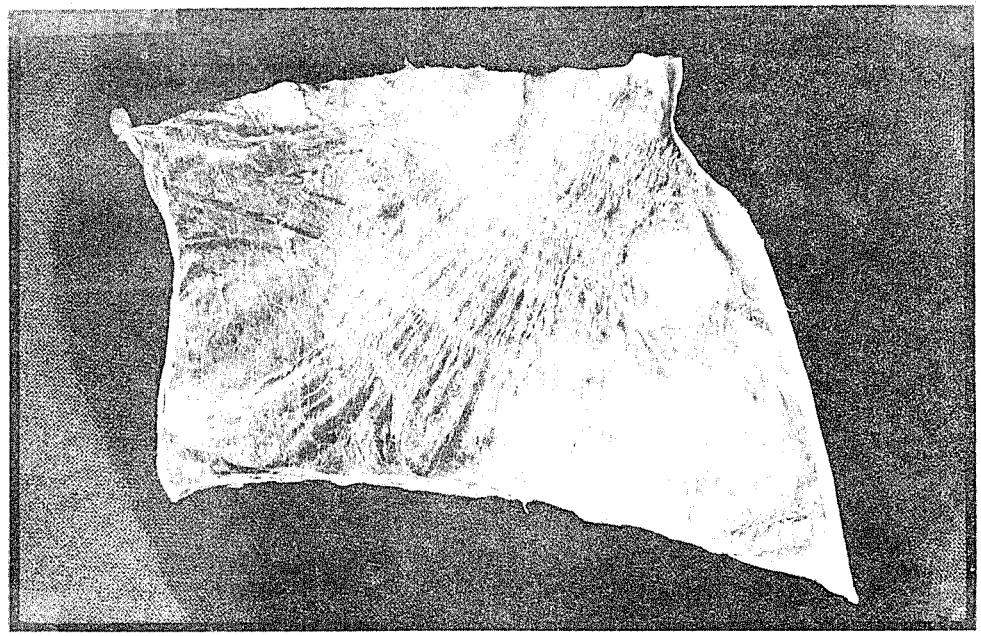
FIG. 1 shows the parietal side of a sheet of tanned bovine pleura produced in accordance with the invention.

In a typical process for producing a biomaterial in accordance with the invention, a sheet of parietal pleura obtained fresh from an abattoir is laid out flat with a single layer of gauze covering its smooth (visceral) surface. The pleura is transported in saline to a laboratory where it is stretched and cleansed of all excessive tissue to result in a uniform membrane 50–150 micron in thickness. This may be achieved by stretching the pleura on a board of cork or other suitable material under clean conditions, pinning it at the edges, and removing excess tissue with surgical instruments and subsequent treatment with ether, chloroform or other fat solvents or dispersants.

The stretched and cleaned pleura, still pinned to the supporting board, is then washed in saline and immersed in a bath of tanning solution. The tanning solution may typically be buffered glutaraldehyde between 2–8 pH, having a concentration of 0.5% to 5% by weight and the pleura may be immersed for periods varying from 15 minutes to 72 hours depending on the final configuration and integrity required. This treatment renders the product non-antigenic and sterile. It also imparts additional strength.

Properties of material such as permeability, strength and biodegradability can be greatly varied by controlling tanning (concentration, pH and duration) and by subsequent treatment. Weak biodegradable materials can be obtained by appropriate tanning followed or preceded by treatment with enzymes such as trypsin, by irradiation, mechanical perforation with spikes, perforation by laser beam or electron beam etching. On the other hand the material would be subjected to a full glutaraldehyde treatment in cases where maximum strength and non-biodegradability was required, for example for patches in the vascular system, hernial defect repair or for tendon repair.

The material can be rendered sterile by the glutaraldehyde treatment by irradiation or in some instances by treatment with ethylene dioxide.

The tanned and sterilised material may be stored in a 50% alcohol solution. Alternatively it may be stored in dried form and be reconstituted with physiological saline prior to use. As another alternative it could be stored in a phosphate buffered saline so as to be in a similar state as physiological plasma.

The following experimental procedures have been carried out to evaluate use of biological material produced in accordance with the present invention.

Experiment 1: Evaluation of Tanned Bovine Pleura in Sheep as a Surgical Dressing

| DOG | L. ATRIUM | R. ATRIUM | PULMONARY OUTFLOW | PERICARDIUM | DURATION |
|---|---|---|---|---|---|
| 1 | 2 cm × 2 cm | 2 cm × 2 cm | | 5 cm × 10 cm | 6 months |
| 2 | 1.5 cm × 1.5 cm | 1.5 cm × 1.5 cm | | 3 cm oval | 3 months |
| 3 | 0.75 cm × 0.75 cm | | 1.5 cm × 1.75 cm | 3 cm × 4 cm | 3 months |
| 4 | 2 cm × 2 cm | | 3 cm × 3 cm | 6 cm × 4 cm | 3 months |
| 5 | 3 cm × 3 cm | | 2.5 cm × 2.5 cm | 4 cm × 4 cm | 3 months |

10 cm × 10 cm wounds were created in three anaesthetised sheep by excising the skin. These wounds were covered by suturing 2.5% glutaraldehyde treated bovine pleura stored in alcohol. The pleura itself was sewn in place. The animals were followed up to three months during which time the material functioned as a satisfactory surgical dressing. There was no shrinkage, no scar formation and no infection. The material was not incorporated or degraded and it was concluded that even better results could be obtained if the pleura were subjected to less tanning and/or irradiation treatment to make it more biodegradable.

Figure 2:
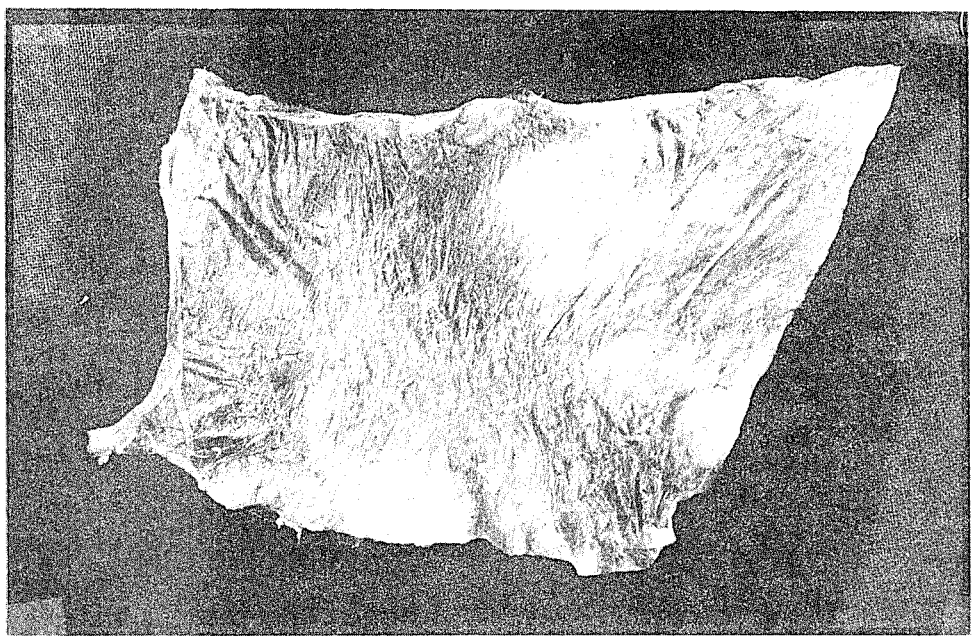
FIG. 2 shows the visceral side of the same sheet of material.
Figure 3:
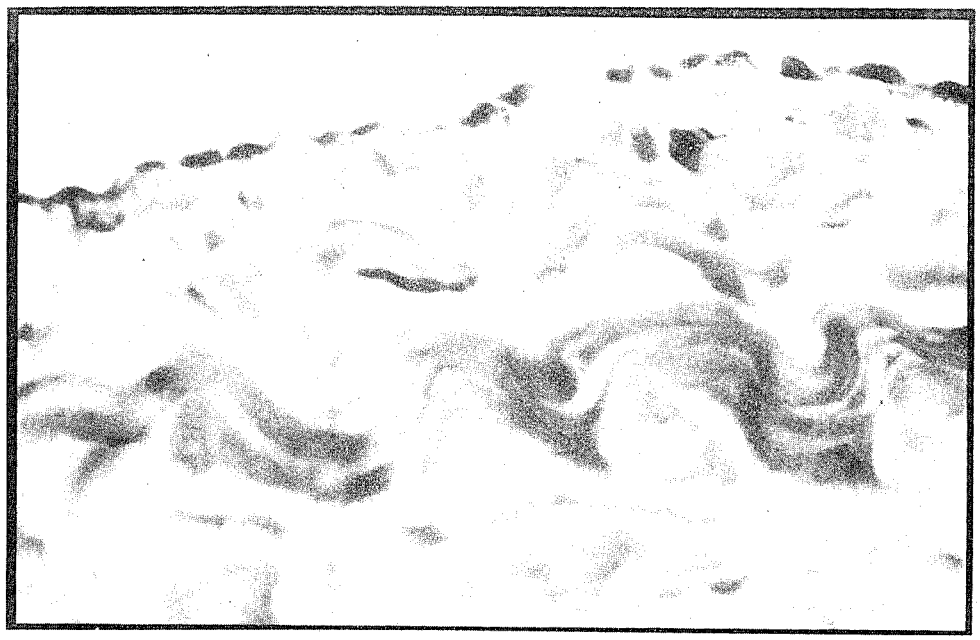
FIG. 3 is a reproduction of a photomicrograph showing a section through a sheet of tanned bovine pleura.

Experiment 2: Evaluation of Tanned Bovine Pleura in Dogs as Haemocompatible Biomaterial and as Patch Replacement for Pericardium Implantation procedures were performed in five dogs using an implant material prepared by tanning bovine parietal pleura tanned in 2.5% glutaraldehyde by weight/volume for 72 hours buffered to an alkaline pH of 7.4. This material is illustrated in FIGS. 1 to 3 of the accompanying drawings. FIG. 1 shows the parietal side and FIG. 2 the visceral side after tanning and FIG. 3 is a photo-micrograph showing a mesothelial cell covering on the visceral surface of the material overlaying an inner structure of collagen fibres.

All dogs, of mixed breeds, subjected to the procedure weighed 14 to 25 kg. They were premedicated with atropine sulphate 0.05mg/kg and acetylpromazine 0.1 mg/kg subcutaneously. General anaesthetic was induced with thiopentone sodium or methohexital sodium and maintained with a mixture of nitrous oxide, halothane and oxygen.

The anaesthetised dogs were placed in the right lateral position, prepared and draped, and a left transcostal thoracotomy via the fourth left intercostal space was performed. In all five dogs a pericardial defect and left atrial appendage amputation was carried out. The defects were repaired with a patch of the tanned pleura. The pleura was sewn with 6/0 prolene to the defects with the visceral surface contacting blood and myocardium. Two of the dogs also had their right atrial appendage amputated and the defect repaired with a pleural patch. In three of the dogs the pulmonary outflow tract was incised longitudinally and a gusset of pleura was sewn in with the visceral surface contacting blood. At the end of the procedure the wound was closed in layers and the chest was drained.

All five dogs survived the procedure. Four of the five dogs were euthanased electively at three months and the one remaining dog was euthanased at six months. All pleural patches, from various sites, were collected and fixed in glutaraldehyde and subsequently examined histologically.

The above procedures are summarised in the following table:

The results of the examination were as follows:

1. Atrial Patches both Left and Right

All atrial patches, except one left atrial patch, were found shrivelled with the surrounding atrial material closing over to heal the wounds. One atrial patch that did not shrivel had a smooth shiny blood contact surface. The external surface was relatively adhesion free. Histologically, the collagen architecture was preserved. The blood contact surface showed "endothelial-like" cells.

2. Pulmonary Outflow Tract Gussets

The pulmonary outflow tract gussets were all identified. They did not exhibit any dilatation or contraction that was obvious. The blood contact surface was again smooth and shiny. Histologically the collagen architecture was preserved with "endothelial-like" cells in the flow surface.

3. Pericardial Patches

All pericardial patches were identified. The healing to the rest of the pericardium was good. There were some adhesions on the parietal surface to the surrounding lung tissue. The visceral pericardial surface was largely smooth and non-adherent to the myocardium.

Figure 4:
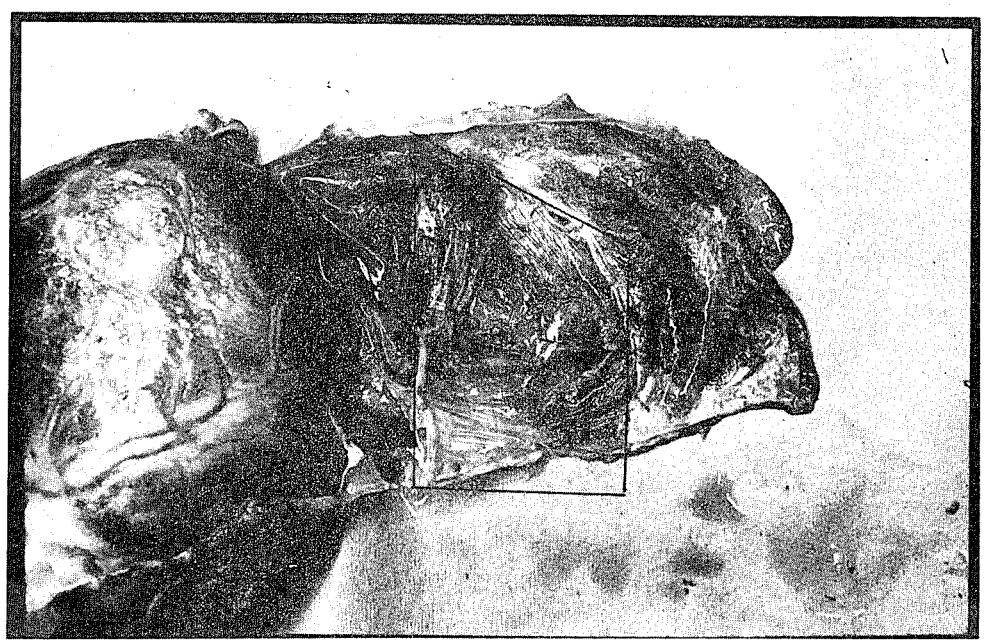
FIG. 4 shows a pericardial patch recovered after six months implantation in a first dog.
Figure 5:
FIG. 5 illustrates a pericardial patch recovered after three months implantation in another dog.
Figure 6:
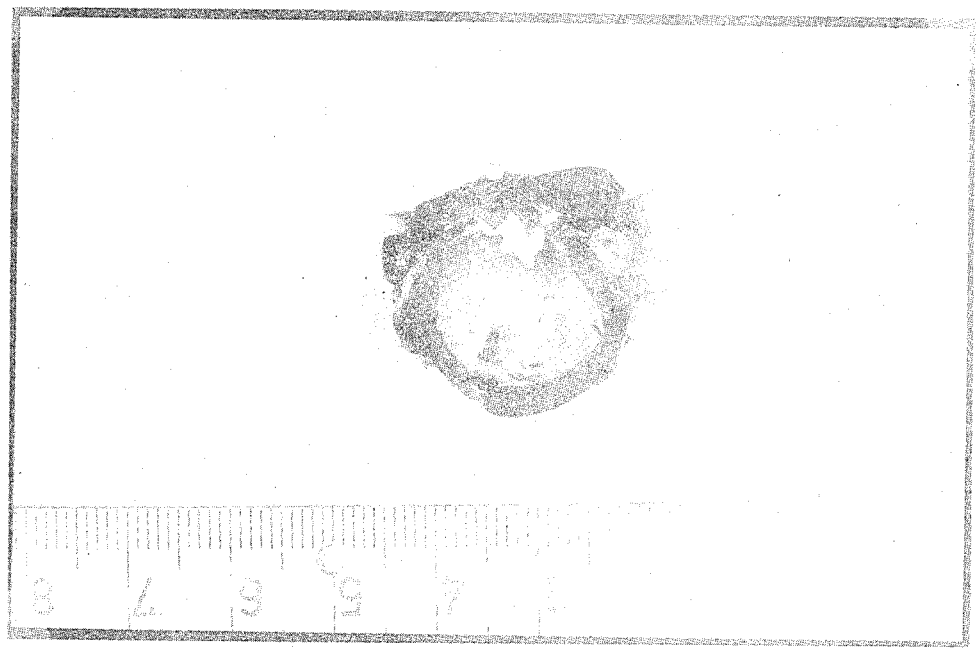
FIGS. 6 and 7 show a left atrial patch and a pulmonary outflow patch recovered after three months implantation in another dog.
Figure 7:
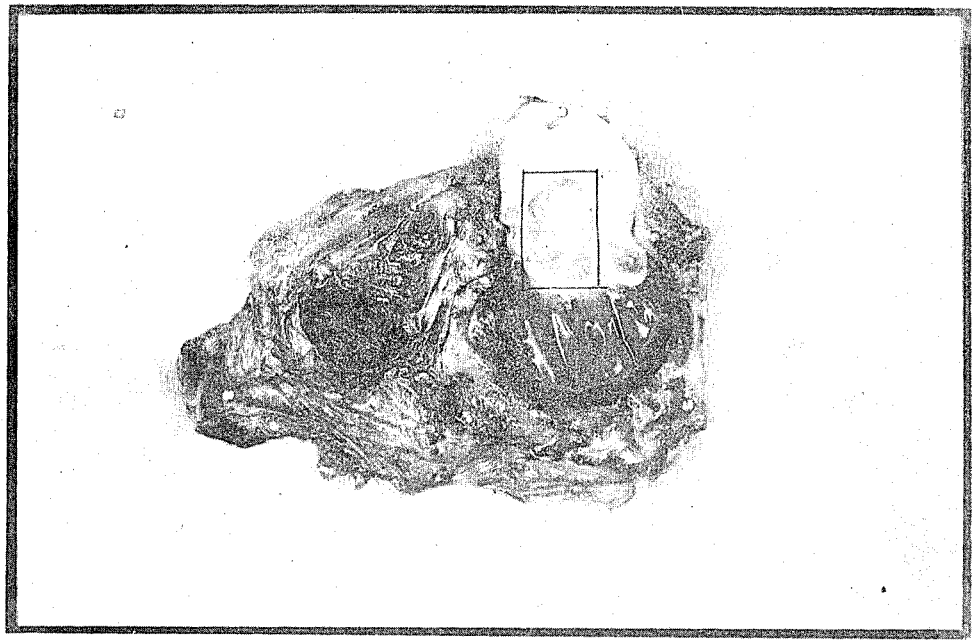
Figure 8:
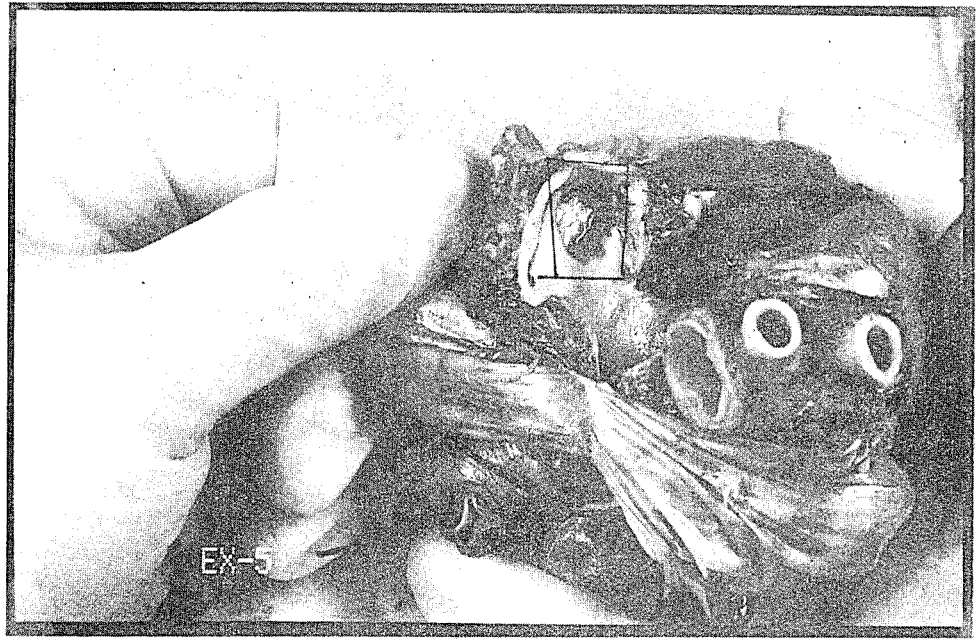
FIG. 8 illustrates a pulmonary outflow patch recovered after three months implantation in a further dog.

The above results are illustrated by FIGS. 4 to 10. FIG. 4 illustrates the pericardial patch after six months implantation in dog no. 1. FIG. 5 shows the pericardial patch reflected off the left ventricular epicardium of dog no. 3 after three months implantation. FIG. 6 shows the left atrial patch after three months implantation in dog no. 4 and FIG. 7 illustrates the pulmonary outflow patch from the same dog. FIG. 8 shows the pulmonary outflow patch of dog no. 5 at three months.

Figure 9:
FIG. 9 is a reproduction of a photomicrograph through the junction of the pulmonary artery and the pulmonary outflow patch of FIG. 7.
Figure 10:
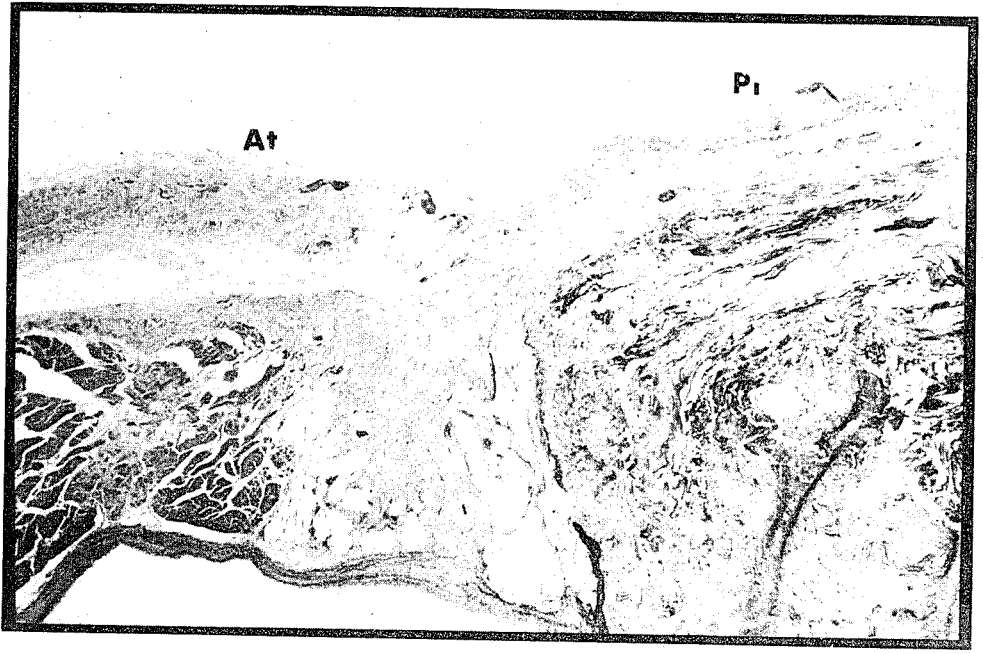
FIG. 10 is a reproduction of a photomicrograph showing a section through the junction of the left atrium and the atrial patch of Figure.

FIG. 9 shows the junction of the pulmonary artery (Pa) and the pulmonary outflow patch (Pl) from dog no. 4. "Endothelial-like" cells can be seen to extend from the pulmonary artery over the pleura patch. FIG. 1 shows the appearance at the junction of the left atrium (At) with the pleural patch (Pl) in dog no. 4 showing a smooth transition from left atrial tissue to the tissue of the implant.

The above results demonstrate that tanned bovine pleura can be both a successful biological patching material and a successful blood contact material.

Experiment 3: Evaluation of Tanned Bovine Pleura in Rats as a Surgical Dressing

In five male hooded wistar rats, weighing approximately 300 grams each, under general anaesthetic, a 2cm diameter full thickness skin defect was created on the left lateral chest wall. The tanned bovine pleura was cut to size and draped over the defect to cover the exposed panniculus carnosus, with the visceral surface contacting the wound. The wound was dressed with paraffin gauze, and the chest was surrounded with plaster bandage. All rats survived the procedure and were then observed for fifteen days. The plaster casts were removed from the fourth day to the fifteenth day. The bovine pleura in this study was tanned in 2.5% glutaraldehyde by weight/volume for 72 hours, buffered to an alkaline pH.

Measurements of the tanned bovine pleural surgical dressing were made at the time of removal of the plaster casts.

The results of these tests were as follows:

| RAT | DAY | DIMENSIONS (mm) | OBSERVATIONS |
| --- | --- | --- | --- |
| 1 | 4 | 20 × 20 | No change |
| 2 | 7 | 20 × 20 | No change |
| 3 | 11 | 22 × 20 | No change |
| 4 | 14 | 15 × 13 | Diminished |
| 5 | 15 | Not Known | Cast fell off and dressing lost |

In three of the five rats between four to eleven days there was no diminution in size, and in one rat there was a slight shrinkage in size. In one rat the "dressing" was lost and no assessment could be made.

Within 24 hours of removal of the casts the dressings dehydrated and were cleaned by the rats.

The above test results provide a further indication that tanned bovine pleura can operate satisfactory as a biosurgical dressing.

INDUSTRIAL APPLICABILITY

The above described results indicate that material produced in accordance with the present invention may have wide application in surgical treatments for the repair of defects in the body, including use as implants or grafts which must provide a blood contact surface.

I claim:

1. A biomaterial comprising a sheet of animal parietal pleura which has been subjected to glutaraldehyde tanning.
2. A material as claimed in claim 1 wherein the pleura is bovine pleura.
3. A method of producing the biomaterial of claim 1 comprising subjecting a sheet of animal parietal pleura to glutaraldehyde and tanning said sheet to provide a sheet of glutaraldehyde tanned animal parietal pleura.
4. A method as claimed in claim 3 wherein the pleura is bovine pleura.
5. A method as claimed in claim 3 wherein the pleura is stretched and cleansed of excessive tissue to result in a membrane of substantially uniform thickness prior to tanning.
6. A method as claimed in claim 3 wherein the pleura is tanned in a solution of buffered glutaraldehyde of between 2-8 pH having a concentration of 0.5%-5% by weight and is immersed in the solution for a period within the range 15 minutes to 72 hours.
7. A method of treating a living human patient comprising applying a sheet of animal parietal pleura of claim 1 which has been subjected to glutaraldehyde tanning as a surgical graft or as a dressing to the patient.
8. A method of treating a living human patient comprising applying to the patient the biomaterial produced by the method claimed in claim 3 as a surgical graft or as a dressing.
9. A method as claimed in claim 7, comprising positioning the visceral surface of the pleura to provide a blood contacting surface.
10. The biomaterial as claimed in claim 1 wherein the visceral surface of the pleura provides a blood contacting surface.
11. A shelf storable surgical graft for a living human patient adapted to support epithelial or endothelial growth composed of the biomaterial of claim 1.
12. A shelf storable surgical dressing for a living human patient adapted to support epithelial or endothelial growth composed of the biomaterial of claim 1.

* * * * *